(12) United States Patent
Gagnon et al.

(10) Patent No.: US 8,378,305 B2
(45) Date of Patent: Feb. 19, 2013

(54) MODULAR MULTI-GEOMETRY PET SYSTEM

(75) Inventors: Daniel Gagnon, Twinsburg, OH (US); Douglas B. McKnight, Willoughby, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 241 days.

(21) Appl. No.: 12/935,302

(22) PCT Filed: Mar. 20, 2009

(86) PCT No.: PCT/IB2009/051190
§ 371 (c)(1),
(2), (4) Date: Sep. 29, 2010

(87) PCT Pub. No.: WO2009/125309
PCT Pub. Date: Oct. 15, 2009

(65) Prior Publication Data
US 2011/0024636 A1 Feb. 3, 2011

Related U.S. Application Data (60) Provisional application No. 61/043,742, filed on Apr. 10, 2008.

(51) Int. Cl.
*G01T 1/20* (2006.01)
(52) U.S. Cl. ....................................... 250/362
(58) Field of Classification Search .................. 250/362
See application file for complete search history.

(56) References Cited

U.S. PATENT DOCUMENTS

| | | | |
|---|---|---|---|
| 5,998,792 A | 12/1999 | DiFilippo | |
| 6,774,370 B1 | 8/2004 | Uchida et al. | |
| 7,332,722 B1 | 2/2008 | Tran et al. | |
| 2006/0000983 A1* | 1/2006 | Charron et al. | 250/394 |
| 2006/0027755 A1* | 2/2006 | Tai | 250/363.03 |
| 2006/0186341 A1 | 8/2006 | Ueno et al. | |
| 2008/0029704 A1 | 2/2008 | Hefetz et al. | |

FOREIGN PATENT DOCUMENTS

| | | |
|---|---|---|
| GB | 2058511 A | 4/1981 |
| JP | 63238486 | 10/1988 |

OTHER PUBLICATIONS

Janecek, M., et al.; A Simulation Study for the Design of a Prototype Insert for Whole-Body PET Scanners; 2006; IEEE Trans. on Nuclear Science; 53(3)1143-1149.
Tai, Y-C., et al.; Design Study of a Detector Insert for High Resolution Clinical PET Imaging; 2003; IEEE Trans. on Nuclear Science Symposium Conference; pp. 1714-1717.

* cited by examiner

*Primary Examiner* — David Porta
*Assistant Examiner* — Hugh H Maupin (57) ABSTRACT

When performing positron emission tomography (PET) scanning and image reconstruction, a primary PET system (10) with a primary PET detector array (12) is used to image a patient or subject, and a secondary PET detector array (14) is coupled to the system at specific input points to mitigate unnecessary duplication of system components. The primary system (10) provides PET data processing and reconstruction for the secondary array (14), in addition to the first array (12). An adjustable array (120) includes radially movable detectors (122) and stationary detectors (124) with different crystal resolutions. The movable detectors (122) are alternately positioned with the stationary detectors (124) at a first radius to form a large detector ring, or are positioned at a second, smaller radius without the stationary detectors (124) to form a small detector ring.

28 Claims, 5 Drawing Sheets

MODULAR MULTI-GEOMETRY PET SYSTEM

CROSS REFERENCE TO RELATED APPLICATIONS

This application claims the benefit of U.S. provisional application Ser. No. 61/043,742 filed Apr. 10, 2010, which is incorporated herein by reference.

The present application finds particular application in patient imaging systems, particularly involving patient imaging devices such as positron emission tomography scanners and the like. However, it will be appreciated that the described technique may also find application in spectroscopy systems, other nuclear imaging scenarios, other imaging techniques, and the like.

The wide use of positron emission tomography (PET) imaging in clinical practice underscores the large variation of imaging tasks and object sizes; from low-count, hot-spot imaging (e.g., FDG oncology), to high resolution perfusion imaging (e.g. brain imaging), to low biological contrast low count imaging (e.g., plaque imaging), etc. However, traditional approaches do not permit combinations of the forgoing imaging techniques by a single imaging system.

The overall quality and system performance of a PET scanner is intimately related to and almost entirely defined by the nature and the geometry of its crystal assembly. Important device characterization (as prescribed by standards organizations like NEMA and IEC) such as sensitivity, spatial resolution, energy resolution, timing resolution scatter fraction, etc., are strongly influenced by the crystal assembly. Electronics and other signal acquisition and processing steps have a significant contribution, but device characterization is largely dependent on the fundamental crystal responses. The aspects of the characterization of scanner properties contrasts with, for example, count rate, which is almost entirely defined by electronics alone, and contrast recovery, which is largely defined by correction and reconstruction algorithms.

The foregoing parameters are important in defining the overall quality of a PET scanner, and the images it can produce. Programmable electronics and variations of the various parameters used during correction and reconstruction can be used to adjust the overall imaging performance to the specific tasks.

While crystals and the crystal assembly are one of the most expensive components of a PET scanner, other parts of the system (e.g., electronics, correction system, reconstruction, patient bed and control, merging of the PET information in multimodality systems such as PET/CT or PET/MR, various display and analysis components, temporary storage and archiving, connection to the rest of the hospital network, etc.) have grown so greatly in cost and complexity that they are now the most significant portion development cost.

The present application provides new and improved systems and methods for merging different crystal assemblies into existing multi-modal imaging systems, which overcome the above-referenced problems and others.

In accordance with one aspect, a dual detector positron emission tomography (PET) system includes a primary PET detector array that provides a first set of acquired PET data, a position processor that receives the PET data and processes the PET data to determine positions on the primary detector array at which radiation is detected, and a coincidence binner that receives the processed PET data and defines pairs of events that are associated with common disintegration events. The system further includes a secondary PET detector array that provides a second set of acquired PET data directly to the coincidence binner, and a reconstruction processor that reconstructs the first set of PET data into a first image and reconstructs the second set of PET data into a second image.

In accordance with another aspect, a method of merging multiple PET detector arrays into a single PET imaging system includes receiving a first set of acquired PET data from a primary PET detector array, processing the first set of acquired PET data to determine positions on the detector array on which radiation is detected, and defining pairs of events that are associated with common disintegration events. The method further includes receiving a second set of acquired PET data from a secondary PET detector array at a coincidence binner, and reconstructing the first set of acquired PET data into a first image and the second set of acquired PET data into a second image.

In accordance with another aspect, a PET detector ring includes N detectors that operate at a first resolution at a first position, and M-N detectors that operate at a second resolution when forming a small detector ring at a second position, and at the first resolution when forming a large detector ring with the N detectors at the first position, where M and N are integers.

In accordance with another aspect, a PET detector ring includes a plurality of first detectors having crystals of a first pitch, and a plurality of radially movable detectors having crystals of a second pitch. The first detectors are interleaved with the movable detectors around the ring in a first configuration. The movable detectors are mounted to move radially inward to form a contiguous smaller ring without the first detectors in a second configuration.

In accordance with another aspect, a method of modeling tracer kinetics using a dual-detector PET scanner includes positioning a first PET detector array around a subject, positioning a second PET detector array around a body segment of the subject, and injecting a tracer compound into the body segment. The method further includes scanning the body segment using the second PET detector array, determining an input function that describes tracer uptake kinetics from scan data acquired by the second PET detector array, and scanning the subject using the first PET detector array.

One advantage is that cost is reduced by leveraging existing system hardware and software.

Another advantage resides in variable crystal array size and resolution.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

Figure 1:
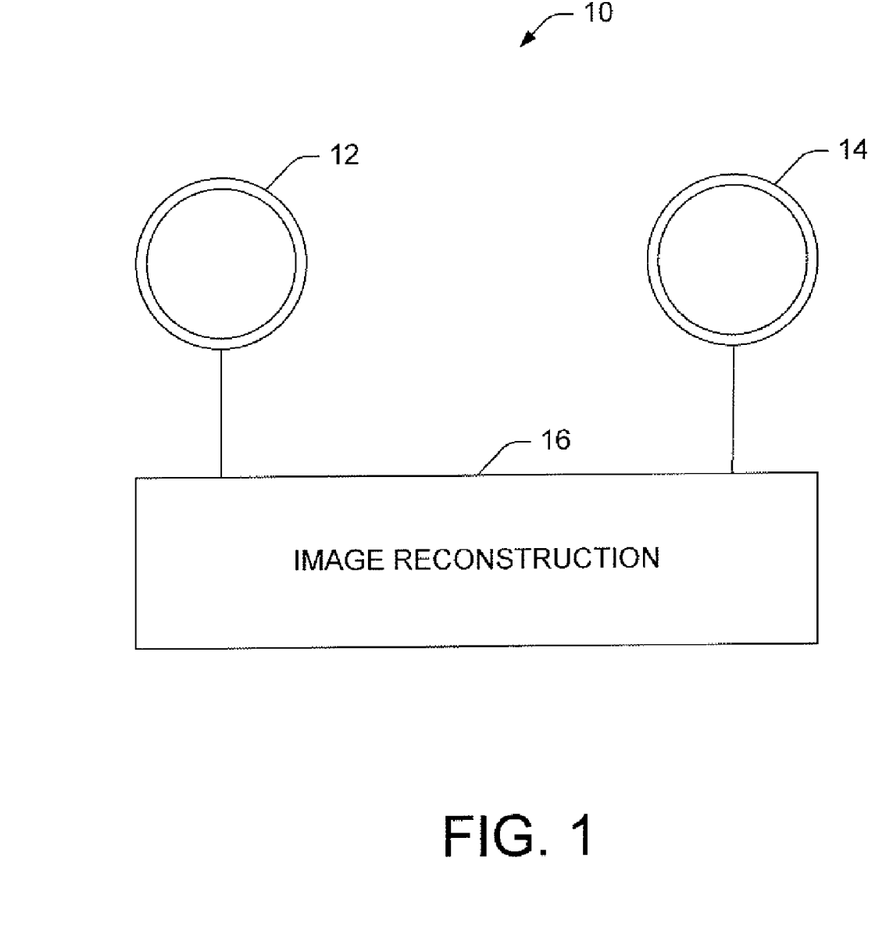
FIG. 1 illustrates a dual PET scanner imaging system for merging different crystal assemblies into a single acquisition and processing system.

FIG. 1 illustrates a dual PET scanner imaging system 10 for merging different crystal assemblies to a single acquisition and processing system. For instance, the system 10 can be employed to merge a primary whole-body PET system with a smaller secondary detector array insert containing different crystal geometry (e.g., for improved spatial resolution) and the minimum set of electronic components (power, sensor, preamplifiers, etc.). In another embodiment, two whole body PET detector systems are merged. By inserting information from the secondary PET detector system or array at pre-specified input points, the system architecture ensures a desired level of quality and thoroughness in the system as well as the maximum amount of sharing of the various components between multiple detector sets. That is, by providing access to the functionality of the system-host for all detector sets, the signal from all detector sets or inserts becomes interpretable.

Accordingly, the system 10 includes a first, or primary, PET detector array 12 and a second, or secondary, PET detector array 14, both of which are coupled to a PET image reconstruction system 16 that acts as the system host. In one embodiment, the second detector array is smaller than the first array, and can be inserted therein to scan a portion of a subject while the first array scans a larger portion of the subject, or the whole subject. For instance, the first array can be a whole-body PET detector array, and the second array can be placed about a patient's arm to acquire tracer flow as a tracer is injected into the patient's arm. The second array can thus acquire PET data for determining an input function describing tracer flow through the patient, which in turn can be used to estimate or predict tracer kinetics throughout the patient. In another embodiment, the second array 14 includes higher resolution crystals that the first array 12, and scans a portion of a subject for which increased resolution is desired. For instance, the first array can include 2×2 mm crystals for scanning an entire subject, and the second array can include 1×1 mm crystals for scanning the subject's brain in higher detail than the first array.

Alternatively, the detector arrays 12, 14 each can include a complete PET scanner with a patient support and the like, as will be appreciated by those of skill. The PET scanners can be placed in the same room or different rooms, and can concurrently or sequentially image different subjects or portions thereof for comparison. The image reconstruction system 16 receives acquired PET data from each scanner and reconstructs respective images. Each scanner or array is optionally associated with an identifier that is transmitted with the PET data therefrom to permit the image reconstruction system to distinguish between signals from crystals in the first array and signals from crystals in the second array.

According to an example, the system 10 is employed in a clinical or preclinical application. For instance, in a preclinical application, a subject is placed in each of the detector arrays 12, 14 and concurrently or alternately imaged to generate images. Such an arrangement can facilitate comparing two subjects for experimental purposes, such as a control subject that has received a placebo and experimental subject that has received a treatment or drug in preclinical trial. According to a related example, the control and experimental subjects can be given a placebo and drug, respectively, while positioned in the detectors, and physiological status can be imaged during the half-life of the drug in the experimental subject while a corresponding physiological status can be imaged in the control subject.

In another example, the second detector array 14 is insertable into the first detector 12 and is employed in a preclinical setting to image a portion or segment of a subject (e.g., a brain or limb) while the first detector 12 images the entire subject or a larger portion thereof.

In yet another example, one or both of the detector arrays are collapsible to accommodate subjects of different sizes. For instance, a rat and a monkey can be concurrently scanned to facilitate generating images for comparison of physiological responses to a stimulus or treatment. According to another embodiment, both detectors can concurrently scan subjects of a first size (e.g., monkeys, dogs, etc.), and can then be collapsed or adjusted to scan subjects of a second size (e.g., rabbits, rats, etc.). Alternatively, the detectors can be employed to scan smaller subjects first, and then enlarged or adjusted to scan larger subjects.

According to an example in which the system 10 is employed for clinical applications, the detector arrays 12, 14 are employed concurrently to image two separate subjects. For instance an organ donor and recipient can be concurrently imaged scanned to generate images for a surgical procedure when time does not permit for two separate scans to be performed sequentially (e.g., by a traditional single detector array scanner). The detector arrays may be of different sizes to accommodate differently sized patients. In one embodiment, the detectors 12, 14 are collapsible and adjustable to accommodate patients of different sizes.

In another example, the second detector array 14 is insertable into the first detector array 12 and is employed in a clinical application to image a portion of a subject (e.g., a patient or animal), while the first detector array 12 images the whole subject. For instance, the second detector array can be positioned around a subject's arm as a tracer is injected into the patient's arm, and an input function can be determined from the image thereof as the tracer traverses the arteries of the arm. The input function can then be applied when analyzing a whole-body image of the patient generated form a scan by the first detector 12.

Figure 2:
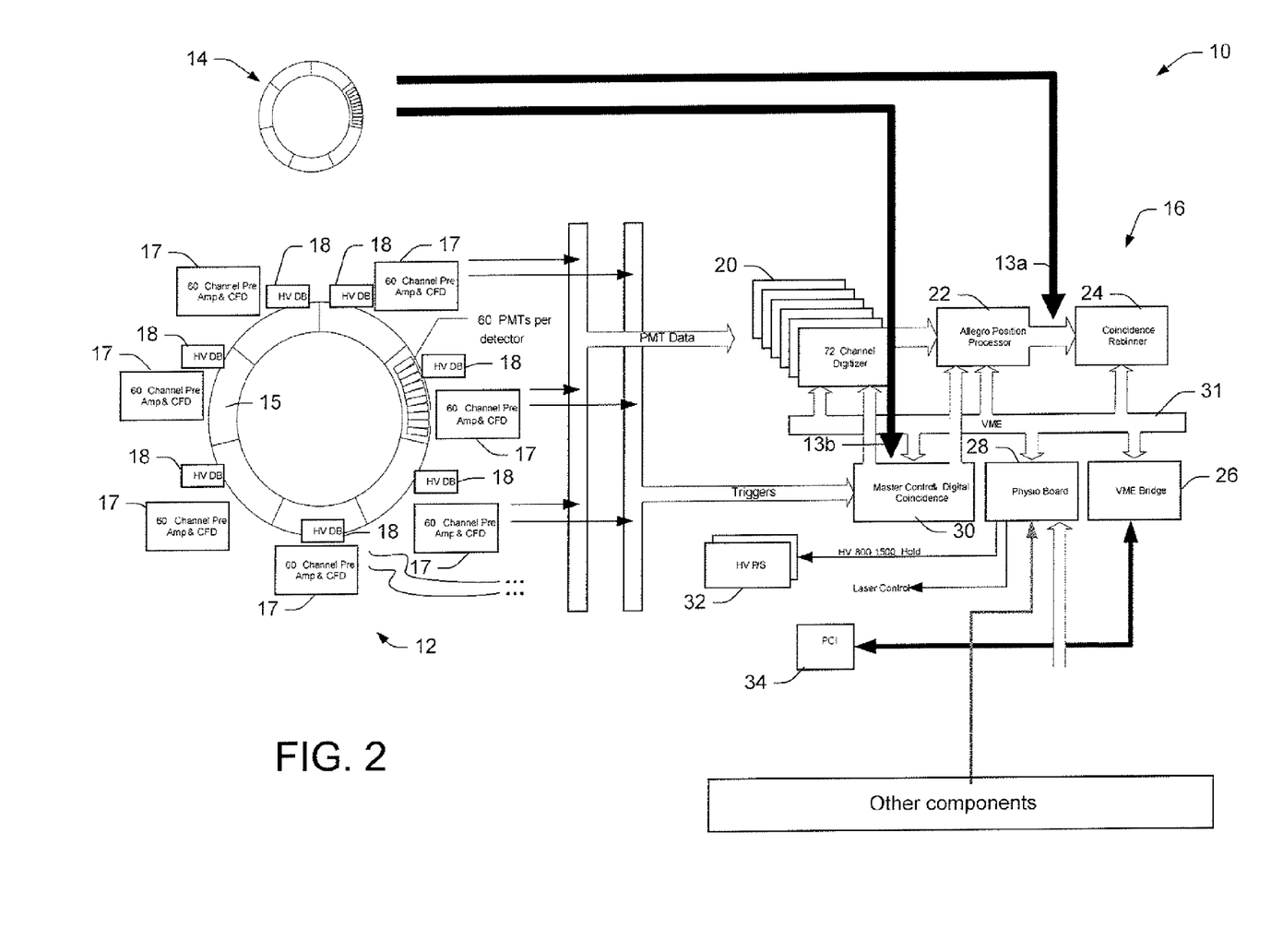
FIG. 2 illustrates an embodiment of the system including the secondary detector array, which transmits data to imaging reconstruction system at specified insertion points, so that the data can be distinguished from primary PET detector data.

FIG. 2 illustrates an embodiment of the system 10 including the secondary detector array 14, which transmits data to imaging reconstruction system 16 at specified insertion points 13a, 13b so that the data can be distinguished from primary PET detector data. In this manner, two or more different detectors having different crystal assemblies can be merged into a single PET scanner system. For example, the primary detector array 12 can be a whole body PET detector and the secondary array 14 can be a cranial detector array. Alternatively, the primary and secondary arrays are both whole body PET detector arrays that can be operated concurrently or sequentially to generate images for comparison. In another embodiment, the different crystal sizes are employed for different sized animal subjects (e.g., monkeys and rats), without requiring a researcher to employ two separate PET scanners.

The system 10 comprises the primary detector ring or array 12 with a plurality of detectors 15, preamplifier and constant fraction discriminator (CFD) components 17, and high voltage detector bars 18. The detectors comprise photomultiplier tubes that transmit detected events to the digitizer 20. In one embodiment, each detector 15 is has 60 PMTs, and the preamplifier and CFD component includes a 60-channel preamplifier. When crystals on the detectors are excited (e.g., when a scintillation event is detected), the PMTs magnify the event and PMT data is transmitted to a digitizer 20 (e.g., a 72-channel digitizer or the like).

The digitizer 20 is coupled to a processor 22, which in turn is coupled to a coincidence rebinner 24. The digitizer, processor, and rebinner are coupled to a virtual machine environment (VME) bridge 26, a physiological board or database 28 that receives monitored physiological signals from a patient, and a master and digital coincidence component 30, all of which are further coupled to each other, by a bus 31. The physiological database 28 is coupled to a cardiac signal component 32, while the VME bridge is coupled to a peripheral component interconnect (PCI) bus 34. Other components included in the image reconstruction system 16 can include an acquisition controller, CT host, PET scanner, and reconstruction processor(s).

The secondary detector ring or array 14 provides output data to the system as input to the coincidence rebinner 24 and to the MCDC component 30. According to an example, the secondary detector is a PET brain array inserted to an existing PET system, and the merging of detector output information can occur at various places depending on the nature of the secondary detector. For instance, a dedicated brain insert can provide a solid-state readout (as opposed to conventional PMT for spatial reasons). Solid state arrays tend to be thinner than PMT arrays and are easier to accommodate in the bore of the primary scanner. Additionally, solid state silicon photomultipliers operate at much lower voltages than PMTs. In this case, the signals are fed into the PET system after processing of the primary detector PMT information by the position processor 22, and are accessed by the coincidence rebinner 24 to define pairs of events that are connected to a same disintegration event. The secondary detector output is also provided to the MCDC component 30, which distinguishes between data received from the primary and secondary detectors.

In one embodiment, the secondary ring 14 provides minimal information to perform a desired imaging task. For instance, the secondary ring may comprise a reduced number of crystals, a sensor, processing electronics, etc., to glean a desired amount of information, with is then fed to the system 10 at the specified insertion points and shared from those points onward during data processing and image generation. According to an example, the primary detector ring includes pixelated crystals and PMTs, while the secondary ring employs Cadmium Zinc Telluride (CZT) crystals or a scintillator and solid state sensor combination. The secondary ring may have a different, generally higher, resolution than the primary ring.

In another embodiment, crystals are provided with unique identities to permit the system 10 to distinguish between detected events in the respective detector inserts. For instance, the crystals of the primary insert may be labeled 0 to N, and the crystals of the secondary insert may be labeled N+1 to M, where N and M are integers. The image reconstruction system 16 distinguishes data transmitted form respective arrays as a function of crystal identifiers. Additionally or alternatively, events detected in different detector rings are time stamped, and the time stamps of detected events are cross-referenced to a time during which a given detector array was in an "on" state to determine whether a given event was detected by the primary detector or the secondary detector.

Alternatively, a physical or virtual switch is provided to control which of the PET detectors and/or arrays is permitted to transmit data to the binning and/or reconstruction components of the image reconstruction system 16 at a given time.

In another embodiment, the two detector arrays are operated concurrently. In this case, a more detailed analysis of rate and system capacity can facilitate distinguishing between primary and secondary data and any enhancement of relevant hardware and software remains desirable over complete duplication of hardware and software.

In yet another embodiment, the detector rings are positioned on a single patient. For instance, the primary array 12 is a whole-body detector that encircles the subject, and the secondary array 14 is positioned about a smaller portion of the patient, such as the subject's head or limb. The secondary array acquires data to detect an initial passage of a tracer through, for instance, an arm of the patient, and the initial passage data is used to generate an input function for kinetic analysis. The secondary array can then be powered down and the primary insert can be powered up to image the whole patient. The secondary insert can be employed in the bore of the primary PET insert system. Alternatively, the secondary insert can be employed in the bore of a multimodal PET/MR system. Optionally, the system 10 operates in list mode, permitting a user to select between respective detector arrays.

Figure 3:
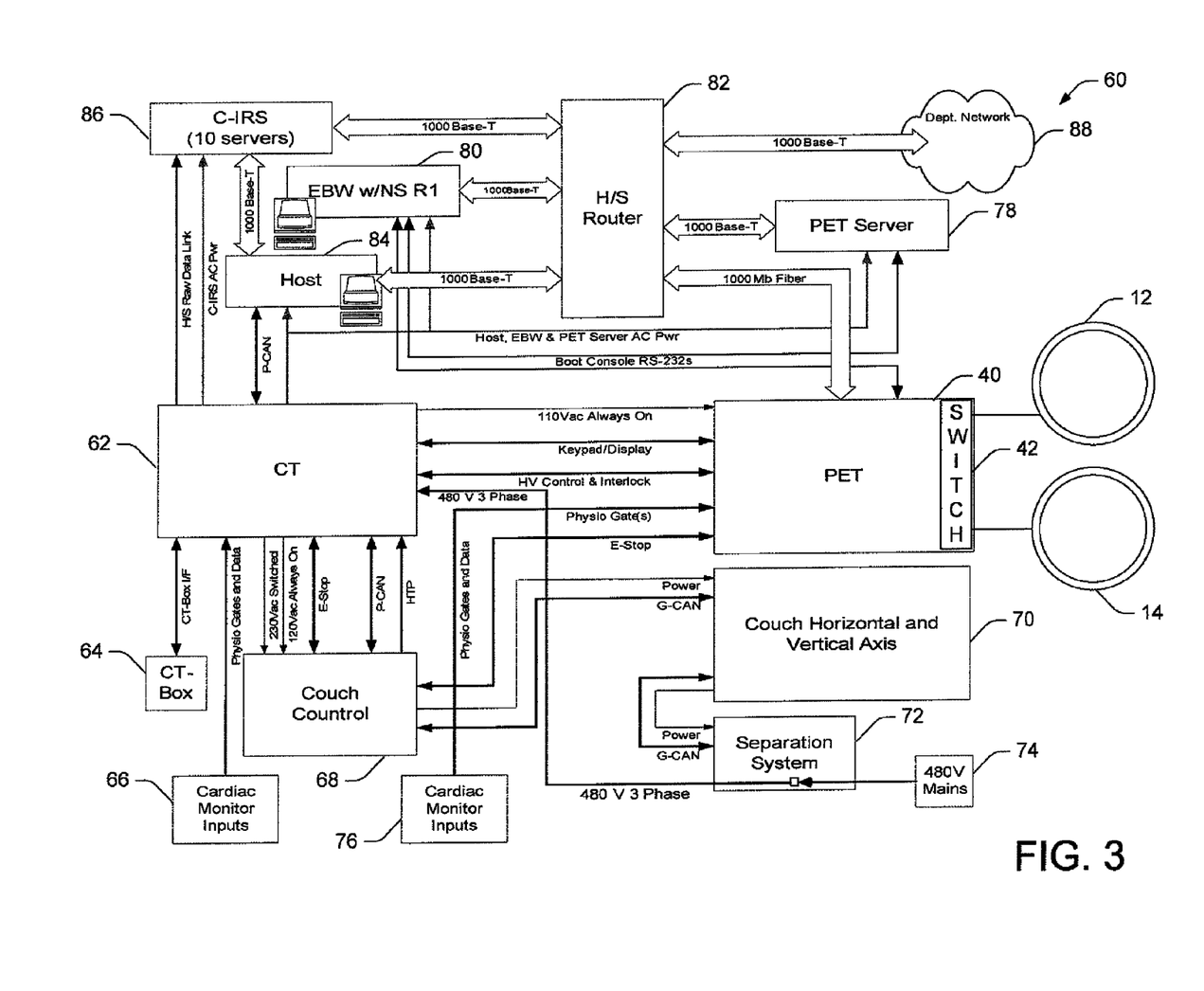
FIG. 3 illustrates a multimodal PET/CT imaging system with dual PET detector arrays and switch that couples the arrays to a PET imaging system.

FIG. 3 illustrates a multimodal PET/CT imaging system 60 with dual PET detector arrays and switch that couples the arrays to a PET imaging system. The system 60 includes a PET scanner 40, which includes a switch 42 for switching between the primary PET detector array 12 and the secondary PET detector array 14. In another embodiment, each of the arrays 12, 14 is housed in an individual PET scanner, and both scanners are coupled to a switch.

The PET detector 40 is coupled to a CT scanner 62, which in turn is coupled to a CT box 64, and to one or more cardiac monitor inputs 66. The CT scanner is further coupled to a patient couch control unit 68. The couch control is connected to the PET scanner and to a couch horizontal and vertical axis (CHVA) controller 70. The CHVA controller is connected to a separation system 72, which in turn is coupled to a 480V main 74 and to the CT scanner 62. Additionally, the PET scanner 40 is coupled to one or more cardiac monitor inputs 76.

A PET server 78 is coupled a workstation 80 such as an Extended Brilliance Workspace (EWB)™ provided by Philips, or the like, which is also coupled to the PET scanner. A hardware/software (H/S) router 82 is coupled to the PET scanner 40, the PET server 78, the workstation 80, a system host 84, an iterative reconstruction server bank 86, and a department network 88. A power line also couples the PET server, the workstation, the CT scanner, and the system host to each other. Additionally, the reconstruction server bank 86 is connected to the host 84 and to the CT scanner, which are further coupled to each other.

Figure 4:
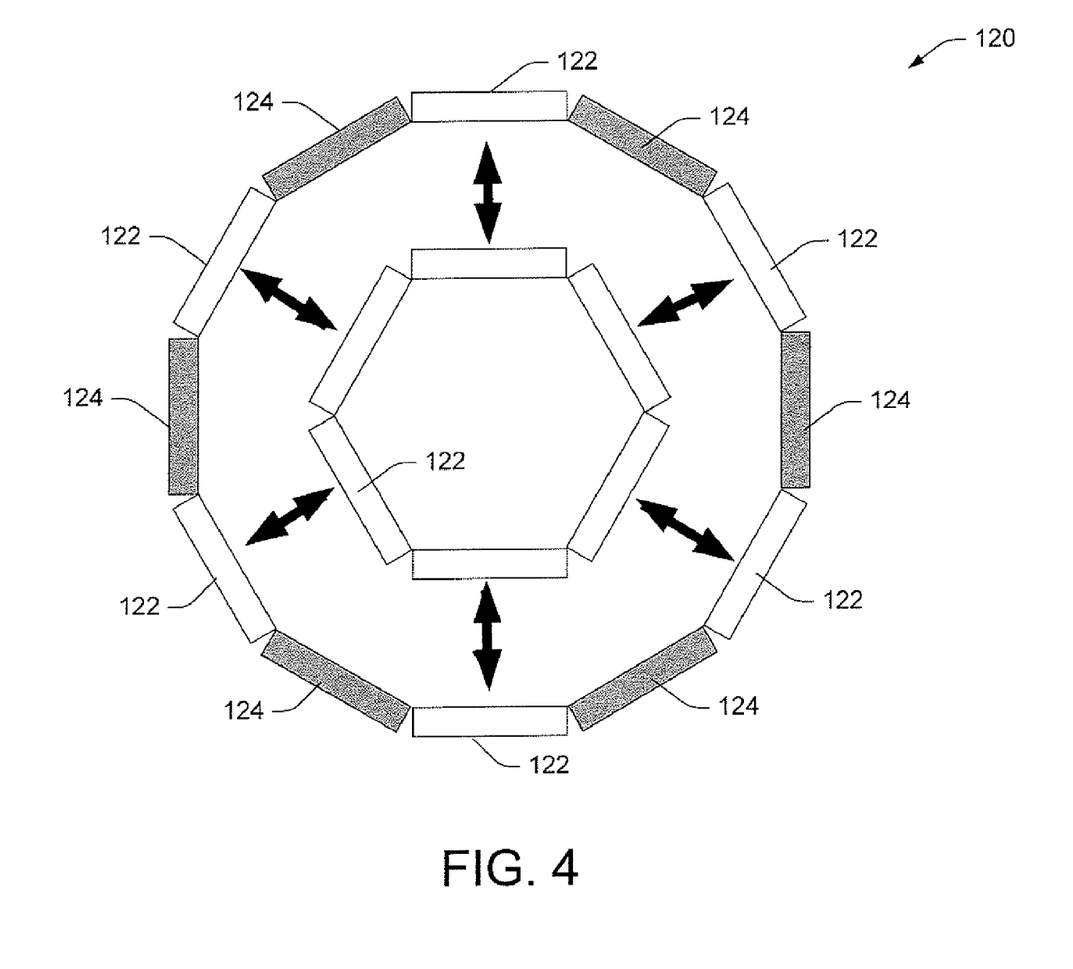
FIG. 4 illustrates a transformable, modular PET detector ring that facilitates providing an additional level of adaptation to the targeted object size and resolution.

FIG. 4 illustrates a transformable, adjustable, modular PET detector ring 120 that facilitates providing an additional level of adaptation to the targeted object size and resolution. The transformable detector geometry facilitates optimally imaging object (animal) of different sizes, and includes a plurality of radially movable detector elements 122 and a plurality of stationary detector elements 124. In one embodiment, the stationary detector elements have approximately half the spatial resolution (crystal pitch) of the radially movable detector elements. By moving the movable elements inward in a circular arrangement, a new, half-size, half-resolution, scanner can be defined. In the example configuration of FIG. 4, the hexagon of high resolution detector elements are brought in the middle from the outer dodecagon.

The smaller diameter detector ring (with the high resolution detectors 122 brought inward) can, for instance, target a 15 cm diameter and 1.5 mm crystal pitch (e.g., for small animals such as mice, rats, etc.). The larger insert ring can target 30 cm in diameter with 3 mm crystal spacing for clinical brain imaging or mid-size animals (e.g., rabbits, monkeys, etc.).

In one embodiment, the high-resolution, radially movable detectors 122 employ 1.5×1.5 mm crystals, and the stationary detector 124 employ 3×3 mm crystals. When in a large-diameter configuration, the high resolution detector collapses or combines four 1.5×1.5 mm crystals (e.g., in a 2×2 orientation) to form one 3×3 mm sensor, the same as the normal-resolution stationary detectors. Coupling and decoupling of crystals on the movable detectors can be accomplished via software/firmware. It will be appreciated that any desired number of stationary detectors can be combined with any desired number of movable detectors, depending on a relative size difference desired between the larger and smaller detector rings. When more than two diameters are selectable, some arrays may be stationary for some diameters and movable for others. Additionally, any desired crystal sizes may be employed to provide the described functionality, which is not limited to crystal surface sizes of 2.25 mm$^2$ and 9 mm$^2$. Furthermore, in one embodiment, the higher resolution crystals on the movable detectors are not summed when they in the large configuration.

In another embodiment, the detector ring 120 functions as the primary detector ring 12 when in a large or expanded orientation, and as the secondary detector ring 14 when collapsed into the small configuration. In this manner, the single collapsible detector ring 120 provides high-resolution scan data in either orientation, and can be adjusted in size to accommodate differently sized subjects, portions of a subject, etc.

In another embodiment, the movable detectors are collapsed inward a predefined distance and are stopped or positioned having gaps therebetween. In this embodiment, a reconstruction processor (not shown) performs post-processing algorithms to account for the gaps and/or any artifacts that may occur. Additionally, the stationary detector arrays may be movable. For example, the stationary detectors can move radially outward to provide enhanced clearance when the movable detectors move radially inward.

Figure 5:
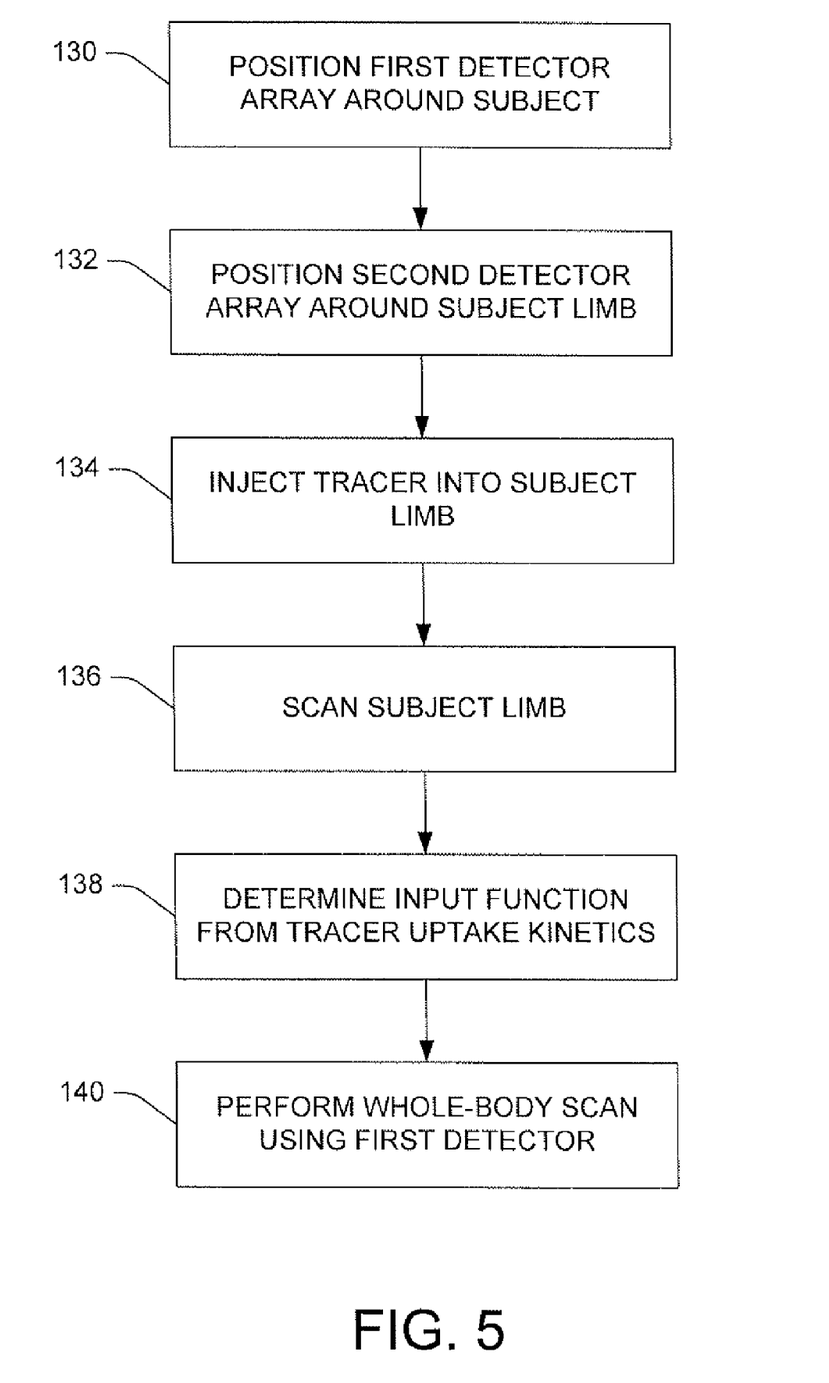
FIG. 5 is an illustration of a method for employing a dual-detector PET scanner to identify an input function for use in analyzing a by first imaging or measuring tracer kinetics as tracer is introduced into a portion of a subject.

FIG. 5 is an illustration of a method for employing a dual-detector PET scanner to identify an input function for use in analyzing a by first imaging or measuring tracer kinetics as tracer is introduced into a portion of a subject. Tracer kinetics are described by time-activity curves relating to tracer uptake in both plasma and tissue. The input or delivery function describes a concentration of original tracer compound in arterial plasma as a function of time, and facilitates estimation of physiological parameters such as blood flow, metabolism, receptor concentration, etc.

At 130, a first detector array is positioned around a subject (e.g., the subject is inserted into a bore of a PET scanner). At 132, a second detector array is positioned about a body segment of the subject, such as an arm. At 134, tracer is injected into the subject's body segment. The body segment is scanned using the second detector at 136. An input function describing a tracer kinetic model is determined at 138, for instance, from the scan data acquired at 136 and/or image data generated therefrom. Once the kinetic model input function is determined, the subject is scanned using the first detector array, at 140.

It will be appreciated that the first and second detector arrays can be coupled to a single image reconstruction system as described with regard to the preceding figures. Additionally, the second detector array may be a collapsible array such as is described with regard to FIG. 4. In another embodiment, the collapsible array is employed as both the first and second arrays, for instance in a collapsed configuration when scanning the subject body segment, and in an expanded configuration when scanning the whole subject.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A dual detector positron emission tomography (PET) system including:
   a primary PET detector array that provides a first set of acquired PET data;
   a position processor that receives the PET data and processes the PET data to determine positions on the primary detector array at which radiation is detected;
   a coincidence binner that receives the processed PET data and defines pairs of events that are associated with common disintegration events;
   a secondary PET detector array that provides a second set of acquired PET data directly to the coincidence binner;
   a reconstruction processor that reconstructs the first set of PET data into a first image and reconstructs the second set of PET data into a second image; and
   an adjustable PET detector ring having a first plurality of radially movable detectors and a second plurality of detectors, the first plurality of detectors being movable to form a larger ring with the second plurality of detectors when positioned at a first position and form a smaller ring comprising only the first plurality of detectors when positioned at a second position that is radially inward from the first position.

2. The system according to claim 1, further including a digitizer that receives the first set of acquired PET data, and receives the second set of acquired PET data directly from the secondary PET detector array, and provides digitized PET data to the position processor for processing, such that the first and second arrays share processing and reconstruction components.

3. The system according to claim 1, further including a digitizer that receives the first set of acquired PET data, and receives the second set of acquired PET data directly from the secondary PET detector array, and provides digitized PET data to the position processor for processing, such that the first and second arrays share processing and reconstruction components.

4. The system according to claim 3, wherein the primary PET detector array and the secondary PET detector array are operated concurrently.

5. The system according to claim 1, wherein the second set of PET data is acquired to monitor a passage of radioactive tracer in a portion of a patient for defining an input function for kinetic analysis.

6. The system according to claim 5, wherein the secondary PET detector array is insertable within at least one of the primary PET detector array or within a bore of a combined PET/magnetic resonance (MR) system.

7. The system according to claim 1, wherein the secondary PET detector array is insertable within at least one of the primary PET detector array or within a bore of a combined PET/magnetic resonance (MR) system.

8. The system according to claim 1, wherein the larger ring is employed as the primary PET detector array and the smaller ring is employed as the secondary PET detector array.

9. The system according to claim 1, wherein the adjustable PET detector ring is employed as the secondary detector array and is insertable into the primary detector array.

10. The system according to claim 1, wherein the second plurality of detectors each comprise a first set of crystals having a first surface area, and wherein the first plurality of detectors each comprise a second set of crystals having a second surface area that is substantially X times as large as the first surface area, where X is greater than 1.

11. The system according to claim 10, wherein crystals in the second set of crystals are combined into sets of X crystals when the first plurality of detectors are at the first position to approximate a size and resolution of crystals on the second plurality of detectors, and are not combined when the first plurality of detectors are at the second position to improve resolution of the smaller ring.

12. The system according to claim 1, wherein the secondary PET detector array is optimized for imaging at least one of a brain or a small animal.

13. The system according to claim 12, wherein the primary PET detector array is optimized for whole-body imaging.

14. A method of merging multiple positron emission tomography (PET) detector arrays into a single PET imaging system, the method including:
receiving a first set of acquired PET data from a primary PET detector array;
processing the first set of acquired PET data to determine positions on the detector array on which radiation is detected;
defining pairs of events that are associated with common disintegration events;
receiving a second set of acquired PET data from a secondary PET detector array at a coincidence binner;
reconstructing the first set of acquired PET data into a first image and the second set of acquired PET data into a second image; and
employing an adjustable PET detector ring having a first plurality of radially movable detectors and a second plurality of detectors, the first plurality of detectors being movable to form a larger ring with the second plurality of detectors when positioned at a first position and form a smaller ring comprising only of the first plurality of detectors when positioned at a second position that is radially inward from the first position, wherein the larger ring is employed as the primary PET detector array and the smaller ring is employed as the secondary PET detector array.

15. The method according to claim 14, further including operating the primary and secondary PET detector arrays concurrently.

16. The method according to claim 15, wherein the secondary PET detector array is insertable into at least one of the primary PET detector array and a bore of a combined PET/magnetic resonance (MR) system.

17. The method according to claim 14, wherein the second plurality of detectors each comprise a first set of crystals having a first surface area, and wherein the first plurality of detectors each comprise a second set of crystals having a second surface area that is substantially X times as large as the first surface area, where X is greater than 1.

18. The method according to claim 17, further including combining crystals in the second set of crystals into sets of X crystals when the first plurality of detectors are at the first position to approximate a size and resolution of crystals on the second plurality of detectors, and not combining crystals in the second set of crystals when the first plurality of detectors are at the second position to improve resolution of the smaller ring.

19. A positron emission tomography (PET) detector ring, including:
N detectors that operate at a first resolution at a first position; and
M-N detectors that operate at a second resolution when forming a small detector ring at a second position, and at the first resolution when forming a large detector ring with the N detectors at the first position, where M and N are integers.

20. A positron emission tomography (PET) detector ring, including:
a plurality of first detectors having crystals of a first pitch;
a plurality of radially movable detectors having crystals of a second pitch;
wherein the first detectors are interleaved with the movable detectors around the ring in a first configuration; and
wherein the movable detectors are mounted to move radially inward to form a contiguous smaller ring without the first detectors in a second configuration.

21. A nuclear imaging system including:
N nuclear imaging detectors that operate at a first resolution at a first position; and
M-N nuclear imaging detectors that operate at a second resolution when forming a small detector ring at a second position, and at the first resolution when forming a large detector ring with the N detectors at the first position, where M and N are integers.

22. The nuclear imaging system according to claim 21, further including:
a digitizer that receives data from the N nuclear imaging detectors, and that receives data from the M-N nuclear imaging detectors; and
a position processor, wherein the digitizer provides digitized nuclear imaging data to the position processor for processing.

23. The nuclear imaging system according to claim 21, wherein the N nuclear imaging detectors and the M-N nuclear imaging detectors are operated concurrently.

24. A multimodality imaging system comprising:
a magnetic resonance (MR) system; and
the nuclear imaging system of claim 21 wherein the M-N nuclear imaging detectors are inserted within a bore of the MR system.

25. A nuclear imaging system including:
a plurality of first detectors having crystals of a first pitch;
a plurality of radially movable detectors having crystals of a second pitch;
wherein the first detectors are interleaved with the movable detectors around the ring in a first configuration; and
wherein the movable detectors are mounted to move radially inward to form a contiguous smaller ring without the first detectors in a second configuration.

26. The nuclear imaging system according to claim 25, further including:
a digitizer that receives data from the plurality of first detectors having crystals of the first pitch, and that receives data from the plurality of radially movable detectors having crystals of the second pitch; and
a position processor, wherein the digitizer provides digitized nuclear imaging data to the position processor for processing.

27. The nuclear imaging system according to claim 23, wherein the first detectors having crystals of the first pitch and the radially movable detectors having crystals of the second pitch are operated concurrently.

28. A multimodality imaging system comprising:
a magnetic resonance (MR) system; and
the nuclear imaging system of claim 25 wherein the radially movable detectors having crystals of the second pitch are inserted within a bore of the MR system.

* * * * *